ized Patent

(12) United States Patent
Hatakenaka et al.

(10) Patent No.: US 12,135,361 B2
(45) Date of Patent: Nov. 5, 2024

(54) IMAGE PROCESSING APPARATUS (71) Applicant: CANON MEDICAL SYSTEMS CORPORATION, Otawara (JP)

(72) Inventors: Hiroyuki Hatakenaka, Nasushiobara (JP); Sho Kawajiri, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/665,641

(22) Filed: Feb. 7, 2022

(65) Prior Publication Data
US 2022/0260656 A1    Aug. 18, 2022

(30) Foreign Application Priority Data
Feb. 16, 2021    (JP) .................................. 2021-022379

(51) Int. Cl.
*G01R 33/343* (2006.01)
*A61B 5/00* (2006.01)
*A61B 5/055* (2006.01)
*G01R 33/36* (2006.01)
*G01R 33/54* (2006.01)

(52) U.S. Cl.
CPC ............ *G01R 33/343* (2013.01); *A61B 5/055* (2013.01); *A61B 5/704* (2013.01); *G01R 33/36* (2013.01); *G01R 33/543* (2013.01)

(58) Field of Classification Search
CPC .... G01R 33/343; G01R 33/36; G01R 33/543; A61B 5/055; A61B 5/704
See application file for complete search history.

(56) References Cited

U.S. PATENT DOCUMENTS

| | | | | |
|---|---|---|---|---|
| 10,845,439 | B2* | 11/2020 | Mitsui ................ | G01R 33/3657 |
| 2002/0173717 | A1* | 11/2002 | Rohling ................ | A61B 5/055 600/415 |
| 2009/0021257 | A1* | 1/2009 | Yasuhara ............. | G01R 33/283 324/318 |
| 2009/0182221 | A1* | 7/2009 | Kasugai ................ | G01R 33/28 600/410 |
| 2016/0095581 | A1* | 4/2016 | Yoneyama ........... | A61B 8/4254 600/440 |
| 2016/0310007 | A1* | 10/2016 | Ishida ..................... | A61B 5/742 |
| 2018/0259601 | A1* | 9/2018 | O'Neill ............ | G01R 33/56509 |
| 2018/0314891 | A1* | 11/2018 | Ota ....................... | G01R 33/543 |
| 2019/0313990 | A1* | 10/2019 | Sahbaee Bagherzadeh ................ A61M 5/007 |
| 2021/0052349 | A1* | 2/2021 | Yano ...................... | G16H 40/63 |
| 2021/0121092 | A1* | 4/2021 | Kawajiri ................ | A61B 5/055 |
| 2021/0224634 | A1* | 7/2021 | Chen .................. | G01R 33/5611 |
| 2021/0321963 | A1* | 10/2021 | Manor ................. | A61B 6/4258 |
| 2022/0229127 | A1* | 7/2022 | Kawajiri ............ | G01R 33/3664 |

FOREIGN PATENT DOCUMENTS

JP          04-071536 A       3/1992

\* cited by examiner

*Primary Examiner* — Dixomara Vargas
(74) *Attorney, Agent, or Firm* — Oblon, McClelland, Maier & Neustadt, L.L.P.

(57) ABSTRACT

An image processing apparatus according to an embodiment includes a processing circuitry. The processing circuitry is configured to acquires an image by capturing a subject laid on a table of a magnetic-resonance imaging apparatus with a camera, detects a loop having a possibility of generating an induced current by a magnetic field that is generated by the magnetic-resonance imaging apparatus from the image, and outputs a detection result.

11 Claims, 5 Drawing Sheets

IMAGE PROCESSING APPARATUS

CROSS-REFERENCE TO RELATED APPLICATIONS

This application is based upon and claims the benefit of priority from Japanese Patent Application No. 2021-022379, filed on Feb. 16, 2021; the entire contents of which are incorporated herein by reference.

FIELD

Embodiments described herein relate generally to an image processing apparatus.

BACKGROUND

One problem to be solved by embodiments disclosed in the present specification and the drawings is to reduce a user's load of confirming. However, problems to be solved by the present specification and the drawings are not limited to the above problem. Problems corresponding to respective effects obtained by respective configurations described in embodiments described later can be regarded as other problems.

DETAILED DESCRIPTION

Hereinafter, an image processing apparatus relating to the present embodiment will be explained with reference to the drawings. In the following embodiments, components having common reference symbols perform similar operations, and duplicated explanation will be omitted as appropriate.

First Embodiment

Figure 1:
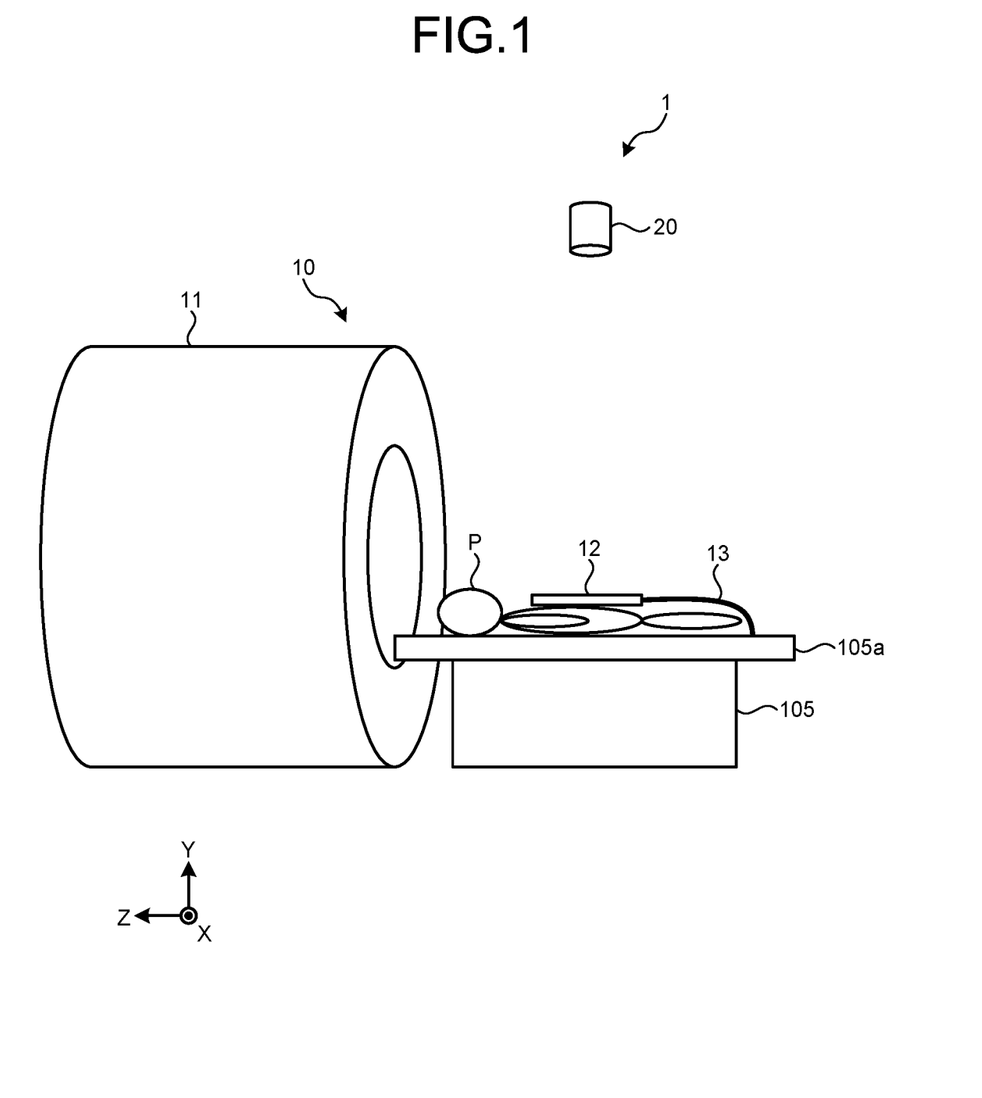
FIG. 1 is a diagram illustrating an example of a configuration of a confirmation support system according to a first embodiment.

FIG. 1 is a diagram illustrating an example of a configuration of a confirmation support system 1 according to a first embodiment. The confirmation support system 1 includes a magnetic resonance imaging (MRI) apparatus 10, and a camera 20. The magnetic-resonance imaging apparatus 10 and the camera 20 are connected to each other by a network such as an in-hospital local area network (LAN). The confirmation support system 1 illustrated in FIG. 1 has the magnetic-resonance imaging apparatus 10 and the camera 20, but the confirmation support system 1 may include more than one unit of the camera 20.

An X-axis, a Y-axis, and a Z-axis in FIG. 1 constitute a device coordinate system unique to the magnetic-resonance imaging apparatus 10. For example, a Z-axis direction coincides with an axial direction of a cylinder of a gradient magnetic field coil 103 (refer to FIG. 2), and is set along a magnetic flux of a static magnetic field generated by a static magnetic-field magnet 101 (refer to FIG. 2). Moreover, the Z-axis direction is the same direction as a longitudinal direction of a bed 105, and is also the same direction as a craniocaudal direction of a subject P laid on the bed 105. Furthermore, an X-axis direction is set along a horizontal direction that is perpendicular to the Z-axis direction. A Y-axis direction is set along a vertical direction that is perpendicular to the Z-axis direction.

The magnetic-resonance imaging apparatus 10 includes the bed 105 on which the subject P is laid, and a frame unit 11 in a substantially cylindrical shape having a hollow in which the subject P is inserted. The magnetic-resonance imaging apparatus 10 receives the subject P inserted in the hollow, and generates a high frequency magnetic field when imaging the subject P. A radio frequency (RF) coil 12 put on the subject P receives an MR signal generated from the subject P. The magnetic-resonance imaging apparatus 10 receives it through a cable 13 of the RF coil 12. The magnetic-resonance imaging apparatus 10 generates an MR image of the subject P laid on a table 105a of the bed 105 based on the received MR signal.

Moreover, the cable 13 of the RF coil 12 may be colored, or may have a pattern, such as geometric pattern, put thereon. When the cable 13 is detected from an image captured by the camera 20, the magnetic-resonance imaging apparatus 10 can detect it easily if it is colored or has a pattern put thereon. When a position in the Y-axis direction of the cable 13 is identified from an image captured by the camera 20, the magnetic-resonance imaging apparatus 10 can identify the position in the Y-axis direction by measuring intervals of lines in a pattern of the cable 13.

The camera 20 is an imaging device that images a moving image or a still image. The camera 20 includes the subject P laid on the table 105a in an imaging region. The camera 20 transmits a captured image to the magnetic-resonance imaging apparatus 10. Moreover, the camera 20 illustrated in FIG. 1 is arranged in an upward direction of the table 105a of the bed 105. However, the camera 20 may be arranged at a different position.

There is a case in which even when the cable 13 forms a loop in a two-dimensional image, the cable 13 does not form a loop in a three-dimensional image. Accordingly, the camera 20 may be arranged in a side direction of the table 105a also, not limited to the upward direction of the table 105a, or may be arranged at another position also. Furthermore, the camera 20 may be an imaging device that images a three-dimensional image that renders an imaging region in three dimension, such as a time of flight (ToF) sensor, and a laser imaging detection and ranging (LiDAR). Moreover, the camera 20 may be an imaging device that is capable of detecting infrared rays. Thus, the camera 20 can capture an image that facilitates recognition of the subject P laid on the table 105a and objects other than the subject P.

In the confirmation support system 1 as described above, the magnetic-resonance imaging apparatus 10 acquires an image captured by the camera 20. Moreover, the magnetic-resonance imaging apparatus 10 determines whether there is a portion in which the cable 13 or the like is looped from an image captured by the camera 20. The magnetic-resonance imaging apparatus 10 notifies of it when a loop of the cable 13 or the like is detected. The magnetic-resonance imaging apparatus 10 is an example of an image processing apparatus.

Next, the magnetic-resonance imaging apparatus 10 will be explained.

Figure 2:
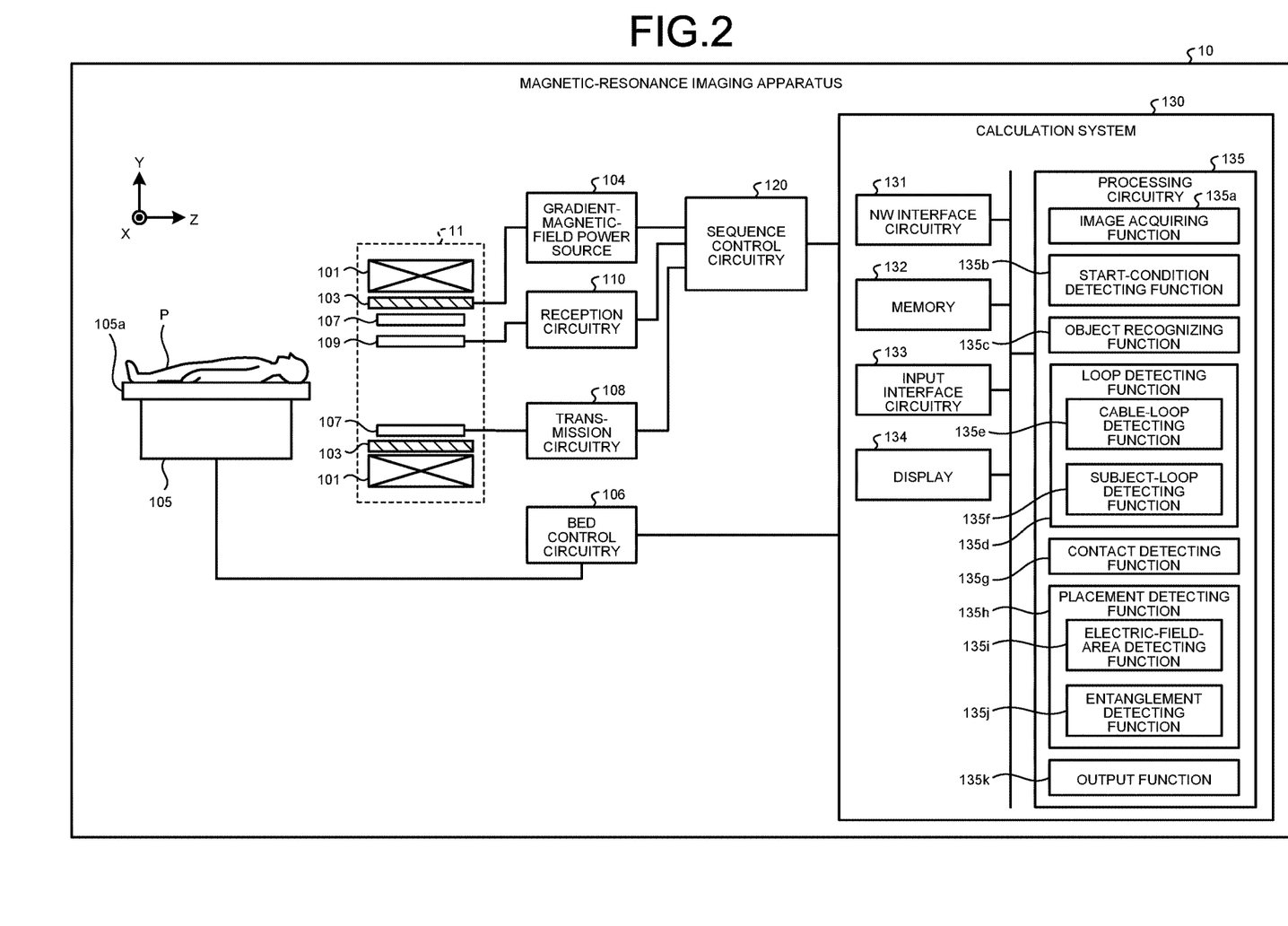
FIG. 2 is a block diagram illustrating an example of a configuration of a magnetic-resonance imaging apparatus according to the first embodiment.

FIG. 2 is a block diagram illustrating an example of a configuration of the magnetic-resonance imaging apparatus 10 according to the first embodiment. The magnetic-resonance imaging apparatus 10 includes the static magnetic-field magnet 101, a static-magnetic-field, power source (not illustrated), the gradient magnetic field coil 103, a gradient-magnetic-field power source 104, the bed 105, a bed control circuitry 106, a transmission coil 107, a transmission circuitry 108, a reception coil 109, a reception circuitry 110, a sequence control circuitry 120, and a calculation system 130.

Note that the configuration illustrated in FIG. 2 is only one example. For example, respective portions in the sequence control circuitry 120 and the calculation system 130 may be configured to be integrated or separated as appropriate. The subject P (for example, human body) is not included in the magnetic-resonance imaging apparatus 10.

The static magnetic-field magnet 101 is a magnet formed in a substantially cylindrical shape having a hollow, and generates a static magnetic field in space thereinside. The static magnetic-field magnet 101 is, for example, a super-conducting magnet or the like, and is excited, receiving a supplied of an electric current from the static-magnetic-field power source. The static-magnetic-field power source supplies an electric current to the static magnetic-field magnet 101. As another example, the static magnetic-field magnet 101 may be a permanent magnet, and in this case, the static-magnetic-field power source may be excluded in the magnetic-resonance imaging apparatus 10. Moreover, the static-magnetic-field power source may be provided separately from the magnetic-resonance imaging apparatus 10.

The gradient magnetic field coil 103 is a coil formed in a substantially cylindrical chape having a hollow, and is arranged inside the static magnetic-field magnet 101. The gradient magnetic field coil 103 is formed with three coils corresponding to respective axes of X, Y, and Z that are perpendicular to one another combined, and these three coils generate a gradient magnetic field, a magnetic field strength of which varies along the respective axes of X, Y, and Z, receiving a supply of an electric current individually from the gradient-magnetic-field power source 104. Furthermore, the gradient-magnetic-field power source 104 supplies an electric current to the gradient magnetic field coil 103 under control of the sequence control circuitry 120.

The bed 105 includes the table 105a on which the subject P is laid, and inserts the table 105a into the imaging port in a state in which the subject P, such as a patient, is laid thereon, under control of the bed control circuitry 106. The bed control circuitry 106 drives the bed 105 to move the table 105a in a length direction and a vertical direction, under control of the calculation system 130.

The transmission coil 107 excites an arbitrary region of the subject P by applying a high frequency magnetic field. The transmission coil 107 is a whole body coil that surrounds, for example, a whole body of the subject P. The transmission coil 107 receives a supply of an RF pulse from the transmission circuitry 108 to generates a high frequency magnetic field, and applies the high frequency magnetic field to the subject P. The transmission circuitry 108 supplies an RF pulse to the transmission coil 107 under control of the sequence control circuitry 120.

The reception coil 109 is arranged inside the gradient magnetic field coil 103, and receives a magnetic resonance signal emitted from the subject P due to an influence of the high frequency magnetic field. Having received the MR signal, the reception coil 109 outputs the received MR signal to the reception circuitry 110.

FIG. 2 illustrates the configuration in which the reception coil 109 is arranged separately from the transmission coil 107, but this is only one example, and configurations are not limited to this configuration. For example, a configuration in which the reception coil 109 serves as the transmission coil 107 also may be adopted.

The reception circuitry 110 generates MR data by subjecting an analog MR signal output from the reception coil 109 to analog/digital conversion. Moreover, the reception circuitry 110 transmits the generated MR data to the sequence control circuitry 120. The AD conversion may be performed in the reception coil 109. Furthermore, the reception circuitry 110 can perform an arbitrary signal processing other than the AD conversion.

The sequence control circuitry 120 drives the gradient-magnetic-field power source 104, the transmission circuitry 108, and the reception circuitry 110 based on sequence information transmitted from the calculation system 130, and thereby performs imaging of the subject P. The sequence information is information in which a procedure to perform imaging is defined. The sequence information includes, for example, strength of an electric current to be supplied to the gradient magnetic field coil 103 by the gradient-magnetic-field power source 104 and timing of supplying the electric current, strength of an RF pulse to be supplied to the transmission coil 107 by the transmission circuitry 108, and timing of applying the RF pulse, timing of detecting the MR signal by the reception circuitry 110, and the like. The sequence control circuitry 120 may be implemented by a processor, or may be implemented by combination of software and hardware.

When MR data is received from the reception circuitry 110 as a result of imaging the subject P by driving the gradient-magnetic-field power source 104, the transmission circuitry 108, and the reception circuitry 110, the sequence control circuitry 120 transfers the received MR data to the calculation system 130.

The calculation system 130 performs overall control of the magnetic-resonance imaging apparatus 10, generation of an MR image, and the like. As illustrated in FIG. 2, the calculation system 130 includes a network (NW) interface 131, a memory 132, an input interface circuitry 133, a display 134, and a processing circuitry 135.

The NW interface circuitry 131 communicates with the sequence control circuitry 120 and the bed control circuitry 106. For example, the NW interface circuitry 131 transmits sequence information to the sequence control circuitry 120. Moreover, the NW interface circuitry 131 receives MR data from the sequence control circuitry 120.

The memory 132 stores the MR data received by the NW interface circuitry 131, k-space data that is arranged in k-space by the processing circuitry 135 described later, image data that is generated by the processing circuitry 135, and the like. The memory 132 is, for example, a semiconductor memory device, such as a random access memory (RAM) and a flash memory, a hard disk, an optical disk, or the like.

The input interface circuitry 133 accepts various kinds of instructions and an information input from an operator. The input interface circuitry 133 is implemented, for example, by a trackball, a switch button, a mouse, a keyboard, a touch pad with which an input operation is performed by touching on an operating surface, a touch screen in which a display screen and a touch pad are integrated, a non-contact input circuit using an optical sensor, a sound input circuit, and the like. The input interface circuitry 133 is connected to the processing circuitry 135, and converts an input operation received from an operation into an electrical signal, to output to the processing circuitry 135. The input interface circuitry 133 is not limited to one having a physical operating part, such as a mouse and a keyboard, in the present embodiment. For example, a processing circuitry of an electrical signal that receives an electrical signal corresponding to an input operation from an external input device that is arranged separately from the calculation system 130, and outputs this electrical signal to a control circuit is also included in examples if the input interface circuitry 133.

The display 134 displays a graphical user interface (GUI) to accept an input of an imaging condition, a magnetic resonance image and the like generated by the processing circuitry 135, and the like under control of the processing circuitry 135. The display 134 is a display device, such as a liquid crystal display, for example.

The processing circuitry 135 controls overall operation of the magnetic-resonance imaging apparatus 10. The processing circuitry 135 includes, for example, an image acquiring function 135a, a start-condition detecting function 135b, an object recognizing function 135c, a loop detecting function 135d, a cable-loop detecting function 135e, a subject-loop detecting function 135f, a contact detecting function 135g, a placement detecting function 135h, an electric-field-area detecting function 135i, an entanglement detecting function 135j, and an output function 135k. In the embodiment, respective processing functions performed by the image acquiring function 135a, the start-condition detecting function 135b, the object recognizing function 135c, the loop detecting function 135d, the cable-loop detecting function 135e, the subject-loop detecting function 135f, the contact detecting function 135g, the placement detecting function 135h, the electric-field-area detecting function 135i, the entanglement detecting function 135j, and the output function 135k are stored in a form of a computer-executable program in the memory 132. The processing circuitry 135 is a processor that implements functions corresponding to respective programs by reading and executing the programs from the memory 132. In other words, the processing circuitry 135 that has read the respective programs is to have the respective functions illustrated in the processing circuitry 135 in FIG. 2.

In FIG. 2, it has been explained that the image acquiring function 135a, the start-condition detecting function 135b, the object recognizing function 135c, the loop detecting function 135d, the cable-loop detecting function 135e, the subject-loop detecting function 135f, the contact detecting function 135g, the placement detecting function 135h, the electric-field-area detecting function 135i, the entanglement detecting function 135j, and the output function 135k are implemented by a single unit of processor, but the processing circuitry 135 may be configured by combining plural independent processors, and it may be configured to implement the respective functions by executing the programs by the respective processors. Moreover, in FIG. 2, it has been explained that a single unit of storage circuit, such as the memory 132, stores programs corresponding to the respective processing functions, but plural storage circuits may be arranged in a distributed manner, and the processing circuitry 135 may be configured to read a corresponding program from an individual unit of storage circuit.

A term "processor" used in the above explanation signifies a circuit, such as a central processing unit (CPU), a graphical processing unit (GPU), an application specific integrated circuit (ASIC), a programmable logic device (for example, simple programmable logic device (SPLD), complex programmable logic device (CPLD)), and a field programmable gate array (FPGA). The processor implements a function by reading and executing a program stored in the memory 132. Instead of storing a program in the memory 132, it may be configured to directly install a program in a circuit of the processor. In this case, the processor reads and executes the program installed in the circuit, to implement the function.

The image acquiring function 135a acquires an image that is obtained by capturing the subject P laid on the table 105e of the magnetic-resonance imaging apparatus 10 by the camera 20. The image acquiring function 135a is one example of an acquiring unit. More specifically, the image acquiring function 135a acquires an image captured by one or more units of the camera 20, an infrared ray image, and a three-dimensional image.

The start-condition detecting function 135b detects a start condition for starting detection of an object to be detected by the loop detecting function 135d, the contact detecting function 135g, and the placement detecting function 135h. The start-condition detecting function 135b is one example of a second detecting unit. More specifically, the start-condition detecting function 135b detects a start condition for starting processing to detect a loop of the cable 13 by the loop detecting function 135d. Furthermore, the start-condition detecting function 135b detects a start condition for starting processing to detect a contact point of the subject P and the cable 13 by the contact detecting function 135g. Moreover, the start-condition detecting function 135b detects a start condition for starting detection processing to detect an object to be detected from a predetermined area by the placement detecting function 135h. The start-condition detecting function 135b detects, for example, that the cable 13 is connected to the magnetic-resonance imaging apparatus 10, or that the table 105a is lifted to be inserted into the imaging port, which is the substantially-cylindrical shaped hollow in the frame unit 11, as a start condition.

The object recognizing function 135c recognizes an object included in an image captured by the camera 20. The object recognizing function 135c is one example of a recognizing unit. For example, the object recognizing function 135c recognizes an object, such as the subject P, the cable 13, a wiring without a risk of burn, an intravenous tube, an air feed tube, and the like. More specifically, the object recognizing function 135c recognizes respective objects based on object characteristic information in which characteristics of respective objects are indicated.

In the object characteristic information, amounts of characteristic indicating temperature, thickness, color, pattern, shape, and the like of the respective objects is defined. The object recognizing function 135c can recognize an object by comparing the object characteristic information with an image of an object included in an image. For example, when a color or a pattern is put on the cable 13, the object recognizing function 135c recognizes the cable 13 of the RF coil 12 that receives a signal generated from the subject P based on the color or the pattern included in an image. The object recognizing function 135c may recognize an object by using plural images captured from different directions, not limited to a single piece of image.

Moreover, the object recognizing function 135c may recognize an object based on an infrared ray image captured by the camera 20 that detects infrared rays. Furthermore, the object recognizing function 135c may recognize an object by using a three-dimensional image captured by the camera 20 that generates three-dimensional images.

In the present embodiment, after the object recognizing function 135c recognizes an object, the loop detecting function 135d, the contact detecting function 135g, and the placement detecting function 135h respectively perform detection of an object to be detected. However, the object recognizing function 135c may recognize an object after the loop detecting function 135d, the contact detecting function 135g, or the placement detecting function 135h detects a corresponding object to be detected.

The loop detecting function 135d detects a loop that has a possibility of generating an induced current by a magnetic field generated by the magnetic-resonance imaging apparatus 10 from an image. The loop detecting function 135d is one example of a first detecting unit. That is, the loop detecting function 135d detects a loop formed by the cable 13 of the RF coil that is used for the magnetic-resonance imaging apparatus 10, or a loop formed by the subject P. Furthermore, the loop detecting function 135d includes the cable-loop detecting function 135e and the subject-loop detecting function 135f.

Figure 3:
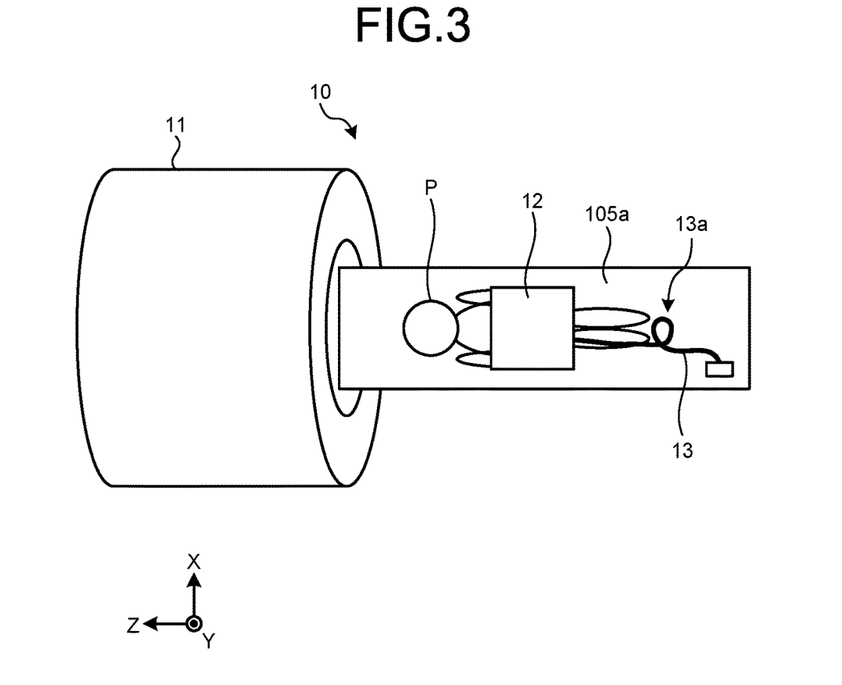
FIG. 3 is a diagram illustrating an example of a subject viewed from above.

The cable-loop detecting function 135e detects a cable loop 13a formed by the cable 13. FIG. 3 is a diagram illustrating an example of the subject P viewed from above. The cable-loop detecting function 135e detects the cable loop 13a formed by the cable 13. In other words, the cable-loop detecting function 135e detects the cable loop 13a that has a possibility of generating an induced current by a high frequency magnetic field generated by the magnetic-resonance imaging apparatus 10. For example, the cable-loop detecting function 135e detects the cable loop 13a by detecting a shape of ring from an image captured by the camera 20 by pattern matching.

Moreover, the cable-loop detecting function 135e may detect the cable loop 13a from an infrared ray image captured by the camera 20 that detects infrared rays. The cable-loop detecting function 135e can easily distinguish the subject P from the cable 13 because of temperature differences. In other words, the cable-loop detecting function 135e can reduce erroneous detection by detecting the cable loop 13a from an infrared ray image.

It is noted that even when a ring shape is formed by the cable 13 in a two-dimensional image, it is not a loop when the cable 13 is not in contact in the Y-axis direction. Therefore, the cable-loop detecting function 135e detects the cable loop 13a based on an arrangement in three-dimensional space of an object, such as the cable 13, included in an image. The cable-loop detecting function 135e identifies an arrangement in the Y-axis direction of the cable 13 based on intervals of a pattern when a pattern is put on the cable 13. That is, the cable-loop detecting function 135e identifies an arrangement in three-dimensional space of the cable 13. When the cable 13 forming a ring overlaps with each other in the Y-axis direction, the cable-loop detecting function 135e detects it as the cable loop 13a. When a three-dimensional image is detected, the cable-loop detecting function 135e may identify an arrangement in three-dimensional space of the cable 13 based on the three-dimensional image.

When detected as a specific object by the object recognizing function 135c, the cable-loop detecting function 135e does not detect it as the cable loop 13a. For example, when an object is recognized as the subject P or a tube by the object recognizing function 135c, the cable-loop detecting function 135e does not detect it even when a loop is formed by the subject P or the tube. Moreover, when an object is recognized as a wiring without a risk of burn by the object recognizing function 135c, the cable-loop detecting function 135e does not detect it as the cable loop 13a.

Furthermore, when recognized as the identical object by the object recognizing function 135c, the cable-loop detecting function 135e detects as the cable loop 13a. That is, the cable-loop detecting function 135e does not detect an object as the cable loop 13a when a loop is formed with more than one object. For example, even when a loop is formed with the cable 13 and the subject P in combination, the cable-loop detecting function 135e does not detect it as the cable loop 13a.

The cable-loop detecting function 135e may detect the cable loop 13a by other methods, not limited to the pattern matching. When an image is input, the cable-loop detecting function 135e may detect the cable loop 13a based on a trained model for detecting the cable loop 13a included in the image. For example, the trained model is generated by supervised learning in which an image and the cable loop 13a included in the image are input as training data.

The subject-loop detecting function 135f detects a subject loop that is a loop formed by the subject P. The subject loop is a loop that is formed as skins of the subject P touch each other. That is, when it is in contact with a towel or an examination gown, the subject-loop detecting function 135f does not detect as a subject loop. For example, the subject-loop detecting function 135f detects a loop by detecting a ring shape from an image captured by the camera 20 by pattern matching.

Moreover, the subject-loop detecting function 135f may detect a loop from an infrared ray image. The subject-loop detecting function 135f can easily distinguish the subject P from the cable 13 because of temperature differences. In other words, the subject-loop detecting function 135f can reduce erroneous detection by detecting the subject P from an infrared ray image. Furthermore, even when a ring shape is formed with the subject in a two-dimensional image, if the subject P is not in contact in the Y-axis direction, it is not a loop. When the subject P forming a ring is in contact in the Y-axis direction, the subject-loop detecting function 135f detects as a subject loop. The subject-loop detecting function 135f detects a subject loop based on an arrangement in three-dimensional space of an object, such as the subject P, included in an image. When a three-dimensional image is acquired, the subject-loop detecting function 135f may identify an arrangement in three-dimensional space of the subject P based on the three-dimensional image.

The subject-loop detecting function 135f may detect the cable loop 13a by other methods, not limited to the pattern matching. When an image is input, the subject-loop detecting function 135f may detect a subject loop based on a trained model for detecting a subject loop included in the image. For example, the trained model is generated by supervised learning in which an image and a subject loop included in the image are input as training data.

The contact detecting function 135g detects a contact between the cable 13 of the RF coil 12 that receives a signal generated from the subject P, and the subject P from an image. The contact detecting function 135g is one example of a third detecting unit. More specifically, the contact detecting function 135g detects a point in which a portion recognized as the subject P by the object recognizing function 135c and a portion recognized as the cable 13 are in contact with each other. That is, when the cable 13 and the subject P are in contact with a towel or an examination gown, the contact detecting function 135g does not detect it as a contact point.

Furthermore, the contact detecting function 135g may detect a loop from an infrared ray image. The contact detecting function 135g can easily distinguish the subject P from the cable 13 because of temperature differences. In other words, the contact detecting function 135g can reduce erroneous detection by detecting a contact point from an infrared ray image.

Even if it looks like in contact in a two-dimensional image, when it is not in contact in the Y-axis direction, the subject P is not in contact with the cable 13. When a three-dimensional image is acquired, the contact detecting function 135g may detect a contact point of the subject P and the cable 13 based on the three-dimensional image.

When an image is input, the contact detecting function 135g may detect a contact point based on a trained model for detecting a contact point included in the image. For example, the trained model is generated by supervised learning in which an image and a contact point of the subject P and the cable 13 are input as training data.

The placement detecting function 135h detects an object to be detected from an electric field area E (refer to FIG. 4) identified by a magnetic field center C (refer to FIG. 4) of the magnetic-resonance imaging apparatus 10, or from a placement prohibited area having a possibility of getting entangled in movement of the bed 105 of the magnetic-resonance imaging apparatus 10. The placement detecting function 135h is one example of a fourth detecting unit. Moreover, the electric field area E is one example of a first area. The placement prohibited area is one example of a second area. The placement detecting function 135h includes the electric-field-area detecting function 135i, and the entanglement detecting function 135j.

The electric-field-area detecting function 135i detects an object to be detected from the electric field area E (refer to FIG. 4) identified by the magnetic field center C (refer to FIG. 4) of the magnetic-resonance imaging apparatus 10. The object to be detected by the electric-field-area detecting function 135i includes the subject P, the cable 13, and the like.

Figure 4:
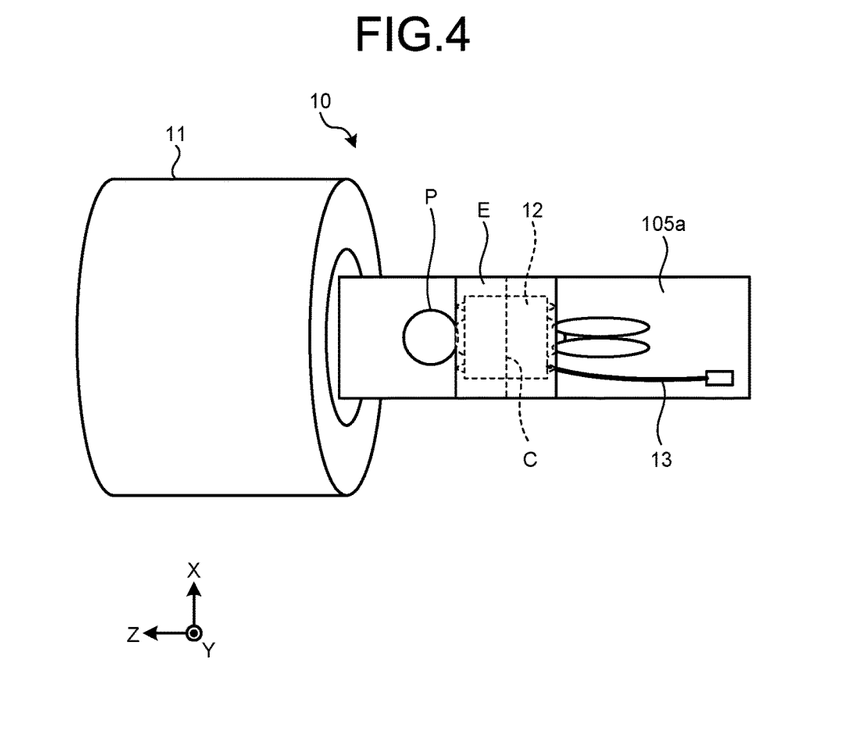
FIG. 4 is a diagram illustrating an example of an electric field area viewed from above.
Figure 5:
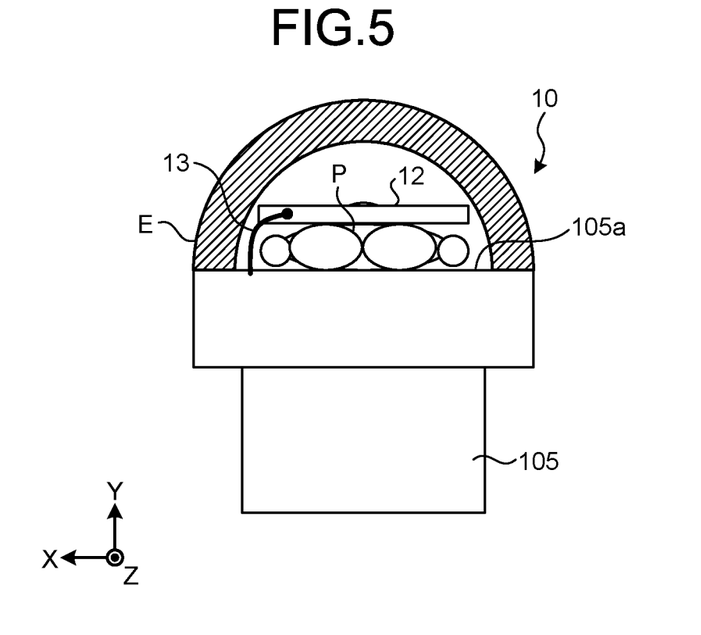
FIG. 5 is a diagram illustrating an example of the electric field area in FIG. 4 viewed from a Z-axis direction.

FIG. 4 is a diagram illustrating an example of the electric field area E viewed from above. FIG. 5 is a diagram illustrating an example of the electric field area E illustrated in FIG. 4 viewed from the Z-axis direction. The frame unit 11 includes the gradient magnetic field coil 103 formed in a substantially cylindrical shape inside the frame unit 11. Moreover, suppose that the magnetic-resonance imaging apparatus 10 generates a high frequency magnetic field such that the magnetic field center C is formed, for example, at a position indicated in FIG. 4 when the subject P is inserted into the hollow of the frame unit 11.

In this case, if an object, such as the cable 13 and the subject P, is placed in the electric field area E, an electric charge is accumulated between the gradient magnetic field coil 103 and the object placed in the electric field area E. In other words, the gradient magnetic field coil 103 and the object placed in the electric field area E function as a capacitor. The object, such as the cable 13 and the subject P, has a possibility of generating heat. Therefore, the subject P can get burned.

For this, the electric-field-area detecting function 135i sets the electric field area E in which placement of an object, such as the cable 13 and the subject P, is prohibited. More specifically, the electric-field-area detecting function 135i sets a range having a first setting distance in the Z-axis direction about the magnetic field center C on the table 105a, and a second setting distance from an edge of the table 105a, to the electric field area E. As illustrated in FIG. 4 and FIG. 5, the electric field area E is formed in a range at a certain distance from an inner wall of the frame unit 11. That is, the electric-field-area detecting function 135i forms the electric field area E in an arch shape. Moreover, because the subject P is laid on the table 105a, it is not to be arranged in a downward direction of the table 105a. Therefore, the electric-field-area detecting function 135i does not form the electric field area E in the downward direction of the table 105a. Furthermore, the first setting distance and the second setting distance can be changed arbitrarily. Furthermore, the magnetic field center C on the table 105a varies per imaging of the subject P. For example, a part of the subject P to be imaged, or a position of the subject P laid on the table 105a varies per imaging of the subject P. Thus, the magnetic field center C on the table 105a varies per imaging of the subject P. Moreover, the electric field E is formed at a position in the Z-axis direction on the table 105a according to a position at which the magnetic field center C is set. That is, the electric field area E is formed at a position in the Z-axis direction according to a feeding amount of the table 105a. For example, when the feeding amount of the table 105a is small, the electric field area E is formed at a position close to the frame unit 11 on the table 105a. On the other hand, when the feeding amount of the table 105a is large, the electric field area E is formed at a position far from the frame unit 11 on the table 105a. The electric-field-area detecting function 135i detects an object to be detected, such as the arm or leg of the subject P and the cable 13, from the electric field area E.

The entanglement detecting function 135j detects an object to be detected from an entanglement hazard area set in advance. The entanglement hazard area is, for example, an area of a gap between the bed 105 and the table 105a, an area outside edges in the longitudinal direction of the table 105a, and the like. Furthermore, the object to be detected is, for example, an intravenous tube. an air feed tube, a wiring, and the like.

The magnetic-resonance imaging apparatus 10 inserts the table 105a on which the subject P is laid into the imaging port of the frame unit 11 when imaging the subject P. If a tube or a wiring is placed in the entanglement hazard area when the table 105a is move, the magnetic-resonance imaging apparatus 10 can entangle the tube or the wiring.

For example, if a tube sticks out to the outside from the edge I the longitudinal direction of the table 105a, the tube can be caught by the frame unit 11 when the table 105a is inserted into the imaging port. In another case, if a tube is placed in a gap between the table 105a and the bed 105, the tube can be drawn into the gap when the table 105a is inserted into the imaging port. Therefore, the entanglement detecting function 135j detects an object to be detected from the entanglement hazard area.

An operating method of the magnetic-resonance imaging apparatus 10 varies per facility. That is, a position at which a medical device is arranged around the magnetic-resonance imaging apparatus 10 differs according to facilities. Therefore, to which position the entanglement hazard area is set may be changed arbitrarily.

The output function 135k outputs a detection result by the loop detecting function 135d, the contact detecting function 135g, and the placement detecting function 135h. The output function 135k is one example of an output unit. More specifically, the output function 135k outputs a detection result in two steps. The output function 135k causes the display 134 to display a detection position image indicating a position of an object to be detected when the object to be detected is detected by the loop detecting function 135*d*, the contact detecting function 135*g*, and the placement detecting function 135*h*. The detection position image is an image in which the detection position of the object to be detected is highlighted in an image showing respective parts of the magnetic-resonance imaging apparatus 10. For example, the detection position image is an image in which an image indicating the object to be detected is superimposed on an image of the magnetic-resonance imaging apparatus 10.

Moreover, when a notification condition is detected, the output function 135*k* notifies that the loop detecting function 135*d*, the contact detecting function 135*g*, or the placement detecting function 135*h* has detected an object to be detected. The notification condition is, for example, an operation of inserting the table 105*a* into the imaging port of the frame unit 11. For example, the operation of inserting the table 105*a* into the imaging port of the frame unit 11 is an operation of designating insertion of the table 105*a* into the imaging port of the frame unit 11, and an operation including insertion of the table 105*a* into the imaging port of the frame unit 11. The operation including insertion of the table 105*a* into the imaging port of the frame unit 11 is, for example, an operation of identifying an organ and the like to be an object to be imaged by the magnetic-resonance imaging apparatus 10. The notification condition is an example, and it may be changed arbitrarily.

The output function 135*k* performs notification by outputting, for example, an alarm sound. Moreover, the output function 135*k* causes the display 134 to display a confirmation image to request to confirm a detection result of the loop detecting function 135*d*, the contact detecting function 135*g*, or the placement detecting function 135*h* in a pop-up or the like. The confirmation image has a confirmation button indicating that it has been confirmed that there is on problem with the detection result. The output function 135*k* hides the confirmation image when an operation indicating that there is no problem with the detection result is accepted. When the confirmation image is hidden, the magnetic-resonance imaging apparatus 10 continues imaging of the subject P. As described, the output function 135*k* can reduce a possibility of missing to check a detection result by restricting imaging of the subject P by the magnetic-resonance imaging apparatus 10.

Figure 6:
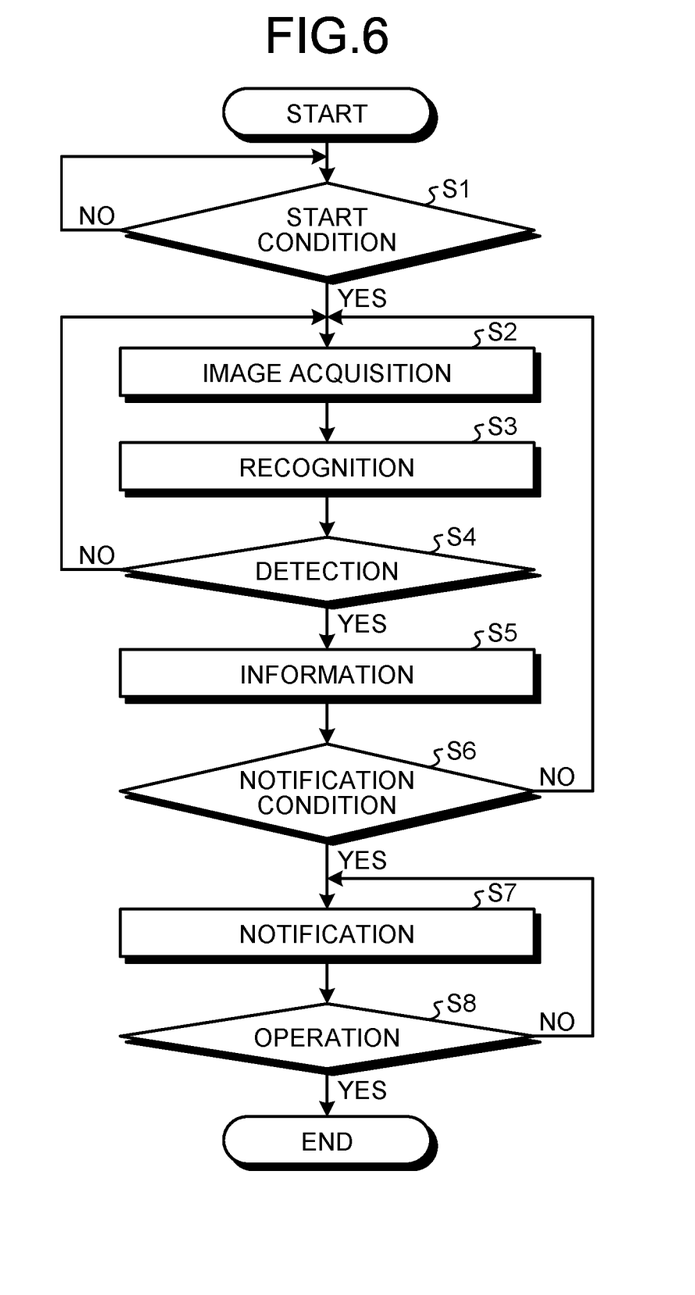
FIG. 6 is a flowchart illustrating an example of confirmation support processing performed by the magnetic-resonance imaging apparatus according to the first embodiment.

Next, confirmation support processing performed by the magnetic-resonance imaging apparatus 10 will be explained. FIG. 6 is a flowchart illustrating an example of the confirmation support processing performed by the magnetic-resonance imaging apparatus 10 according to the first embodiment.

The start-condition detecting function 135*b* determines whether a start condition for starting detection of an object to be detected is detected (step S1). When a start condition is not detected (step S1: NO), the start-condition detecting function 135*b* waits in standby.

When a start condition is detected (step S1: YES), the image acquiring function 135*a* acquires an image captured by the camera 20 (step S2).

The object recognizing function 135*c* recognizes respective objects included in the image acquired by the image acquiring function 135*a* (step S3).

The loop detecting function 135*d*, the contact detecting function 135*g*, or the placement detecting function 135*h* determines whether an object to be detected is detected (step S4). When an object to be detected is not detected (step S4: NO), the image acquiring function 135*a* acquires an image at step S2.

When an object to be detected is detected (step S4: YES), the output function 135*k* informs of a detection result of the loop detecting function 135*d*, the contact detecting function 135*g*, or the placement detecting function 135*h* (step S5). That is, the output function 135*k* causes the display 134 to display a detection position indicating a position at which the object to be detected is detected.

The output function 135*k* determines whether a notification condition for notifying of a detection result is satisfied (step S6). When the notification condition is not satisfied (step S6: NO), the image acquiring function 135*a* acquires an image at step S2.

When the notification condition is satisfied (step S6: YES), the output function 135*k* notifies of it by displaying a confirmation screen to request for confirmation of the detection result on the display 134 (step S7).

The output function 135*k* determines whether a confirmation operation indicating that the detection result has been confirmed is accepted (step S8). When the confirmation operation is not accepted (step S8: NO), the output function 135*k* continues display of the confirmation screen at step S7.

When the confirmation operation is accepted (step S8: YES), the magnetic-resonance imaging apparatus 10 ends the confirmation support processing by hiding the confirmation screen.

As described above, the magnetic-resonance imaging apparatus 10 according to the first embodiment acquires an image of the subject P laid on the table 105*a* of the magnetic-resonance imaging apparatus 10 captured by the camera 20. Moreover, the magnetic-resonance imaging apparatus 10 detects the cable loop 13*a*, a loop of the subject P, a portion that is in contact with the cable 13, a point at which the table 105*a* can entangle the cable 13 or a tube, and the like from the acquired image. The magnetic-resonance imaging apparatus 10 outputs a detection result to a user by displaying it or the like. Therefore, the magnetic-resonance imaging apparatus 10 can reduce a user's load of confirming.

First Modification

In the first embodiment, it has been explained that the magnetic-resonance imaging apparatus 10 includes the image acquiring function 135*a*, the start-condition detecting function 135*b*, the object recognizing function 135*c*, the loop detecting function 135*d*, the cable-loop detecting function 135*e*, the subject-loop detecting function 135*f*, the contact detecting function 135*g*, the placement detecting function 135*h*, the electric-field-area detecting function 135*i*, the entanglement detecting function 135*j*, and the output function 135*k*. However, not limited to the magnetic-resonance imaging apparatus 10, the image acquiring function 135*a*, the start-condition detecting function 135*b*, the object recognizing function 135*c*, the loop detecting function 135*d*, the cable-loop detecting function 135*e*, the subject-loop detecting function 135*f*, the contact detecting function 135*g*, the placement detecting function 135*h*, the electric-field-area detecting function 135*i*, the entanglement detecting function 135*j*, and the output function 135*k* may be provided in another device. For example, the image acquiring function 135*a*, the start-condition detecting function 135*b*, the object recognizing function 135*c*, the loop detecting function 135*d*, the cable-loop detecting function 135*e*, the subject-loop detecting function 135*f*, the contact detecting function 135*g*, the placement detecting function 135*h*, the electric-field-area detecting function 135*i*, the entanglement detecting function 135*j*, and the output function 135*k*

What is claimed is:

1. An image processing apparatus, comprising:
processing circuitry configured to
acquire a three-dimensional image by capturing, with a camera, a subject laid on a table of a magnetic-resonance imaging apparatus;
recognize an object included in the acquired three-dimensional image;
detect, based on a three-dimensional arrangement in the acquired three-dimensional image, a loop having a potential of generating an induced current by a magnetic field generated by the magnetic-resonance imaging apparatus, the loop being either a first loop formed by a combination of the subject and a cable of a radio frequency (RF) coil used in the magnetic-resonance imaging apparatus or a second loop formed by the subject; and
display, on a display, a detection position image in which a first image indicating the detected loop in a highlighted form is superimposed on a second image showing respective parts of the magnetic-resonance imaging apparatus.

2. The image processing apparatus according to claim 1, wherein the processing circuitry is further configured to not detect the loop when recognizing the object as a specific, predetermined object.

3. The image processing apparatus according to claim 2, wherein the processing circuitry is further configured to detect the loop when recognizing multiple objects that are identical objects that form the loop in combination.

4. The image processing apparatus according to claim 2, wherein the processing circuitry is further configured to recognize the cable of the RF coil used in the magnetic-resonance imaging apparatus based on any one of a color and a pattern included in the three-dimensional image.

5. The image processing apparatus according to claim 1, wherein the processing circuitry is further configured to detect the loop from the three-dimensional image captured by the camera, which detects an infrared ray.

6. The image processing apparatus according to claim 1, wherein the processing circuitry is further configured to detect the loop based on an arrangement of the recognized object in three-dimensional space included in the three-dimensional image.

7. The image processing apparatus according to claim 1, wherein the processing circuitry is further configured to detect the loop based on a trained model for detecting the loop when the three-dimensional image is input to the trained model.

8. The image processing apparatus according to claim 1, wherein the processing circuitry is further configured to detect a start condition for starting detection of the object.

9. An image processing apparatus, comprising:
processing circuitry configured to
acquire a three-dimensional image by capturing, with a camera, a subject laid on a table of a magnetic-resonance imaging apparatus;
detect, from the acquired three-dimensional image, direct contact between the subject and a cable of an RF coil that is used in the magnetic-resonance imaging apparatus; and
display, on a display, a detection position image in which a first image indicating the detected contact in a highlighted form is superimposed on a second image showing respective parts of the magnetic-resonance imaging apparatus.

10. An image processing apparatus, comprising:
processing circuitry configured to
acquire an image by capturing, with a camera, a subject laid on a table of a magnetic-resonance imaging apparatus;
detect, based on the acquired image, a tube from an area having a possibility of entanglement in movement of a bed of the magnetic-resonance imaging apparatus; and
display, on a display, a detection position image in which a first image indicating the detected tube in a highlighted form is superimposed on a second image showing respective parts of the magnetic-resonance imaging apparatus.

11. The image processing apparatus according to claim 1, wherein the processing circuitry is further configured to:
output a confirmation image to request to confirm the detection position image, and
hide the confirmation image when receiving an operation indicating that it has been confirmed there is no problem with the detection position image.

* * * * *